(12) United States Patent
Nakayama et al.

(10) Patent No.: US 7,947,007 B2
(45) Date of Patent: May 24, 2011

(54) BUBBLE TRAP

(75) Inventors: Hidetaka Nakayama, Shizuoka (JP);
Mitsuaki Ogihara, Shizuoka (JP);
Kazuhiko Takeuchi, Shizuoka (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 1034 days.

(21) Appl. No.: 11/783,413

(22) Filed: Apr. 9, 2007

(65) Prior Publication Data

US 2007/0239097 A1    Oct. 11, 2007

(30) Foreign Application Priority Data

Apr. 11, 2006  (JP) ................. 2006-109181
Jul. 13, 2006  (JP) ................. 2006-193311

(51) Int. Cl.
*A61M 37/00*    (2006.01)
*A61M 1/00*    (2006.01)

(52) U.S. Cl. ............. 604/6.09; 604/4.01; 604/320

(58) Field of Classification Search .......... 422/44–48; 604/8–10, 5.01, 6.01–6.16, 151–153, 246, 604/249, 317; 137/15.26; 210/247, 304, 210/315, 446

See application file for complete search history.

(56) References Cited

U.S. PATENT DOCUMENTS

| | | |
|---|---|---|
| 3,747,302 A | 7/1973 | Frayssinoux |
| 5,879,624 A | 3/1999 | Boehringer et al. |
| 6,302,860 B1 | 10/2001 | Gremel et al. |
| 2005/0261618 A1* | 11/2005 | Gershowitz ............... 604/4.01 |

FOREIGN PATENT DOCUMENTS

EP    1 344 543 A1    9/2003

OTHER PUBLICATIONS

Extended European Search Report.

* cited by examiner

*Primary Examiner* — Leslie R Deak
*Assistant Examiner* — Philip R Wiest
(74) *Attorney, Agent, or Firm* — Buchanan Ingersoll & Rooney PC

(57) ABSTRACT

A bubble trap for removing bubbles from blood flowing through an extracorporeal circuit includes device body possessing blood inlet and outlet ports, and a negative-pressure chamber at the upper part of the device body that is adapted to be connected to a gas evacuator at a gas outlet port so that a negative-pressure state can be kept therein. Two communication passages provide communication between the gas outlet port and the device body. On the first communication passage, a liquid-repellant or water-repellent filter is provided in a manner crossing the passage. On the second communication passage, a valve member is arranged. Within the device body, a buoyant float is provided. A mechanism is provided to remove bubbles from the blood by the cooperation of the float and the valve member.

4 Claims, 10 Drawing Sheets

US 7,947,007 B2

BUBBLE TRAP

TECHNICAL FIELD

The present invention generally pertains to the removal of bubbles in blood. More specifically, the invention relates to a bubble trap for removing bubbles from blood under extracorporeal circulation.

BACKGROUND OF THE INVENTION

In heart surgery, extracorporeal blood circulation is performed by drawing blood from a vein (vena cava) of a patient through operation of a blood pump and, following gas-exchange in an oxygenator, returning the blood to an artery of the patient.

A bubble trap is typically arranged on the extracorporeal circuit to remove the bubbles mingled in the blood drawn. One example of a bubble trap is disclosed in U.S. Pat. No. 6,302,860. This bubble trap includes a housing and a filter received in the housing. The housing is provided with an inlet port through which blood enters the housing, an outlet port through which the blood in the housing exits, and a bubble outlet port connected to a gas-evacuation device for removing bubbles in the housing under vacuum.

SUMMARY

According to one aspect, a bubble trap comprises a device body possessing an interior, a blood inlet port in the device body communicating with the interior of the device body, a blood outlet port provided in the device body communicating with the interior of the device body, a gas outlet port adapted to be connected to an evacuator which withdraws gas under vacuum, a first communication passage communicating the interior of the device body with the gas outlet port, a second communication passage communicating the interior of the device body with the gas outlet port, and a filter member arranged at the first communication passage which permits passage of gas from the interior of the device body toward the gas outlet port by way of the first communication passage and which prevents passage of blood from the interior of the device body toward the gas outlet port by way of the first communication passage. A movable valve member is arranged in the second communication passage and is positionable in an open position in which the interior of the device body communicates with the gas outlet port by way of the second communication passage and a closed position in which communication between the interior of the device body and the gas outlet port by way of the second communication passage is prevented. A float is positioned in the interior of the device body and is vertically movable in response to a change of a blood level in the device body, and the valve member is connected to the float so that vertical movement of the float causes the valve member to move between the opened and closed positions.

According to another aspect, a bubble trap comprises a device body possessing an interior, a blood inlet port in the device body communicating with the interior of the device body, a blood outlet port provided in the device body communicating with the interior of the device body, a gas outlet port adapted to be connected to a negative pressure source which withdraws gas under vacuum, a first communication passage extending between the interior of the device body and the gas outlet port, a second communication passage extending between the interior of the device body and the gas outlet port, a filter member in the first communication passage which permits passage of gas and prevents passage of blood from the interior of the device body toward the gas outlet port, a float positioned in the interior of the device body and vertically movable in response to a change of a blood level in the device body, and first and second movable valve members in the second communication passage. The first and second movable valve members are connected to the float to move between an open position and a closed position based on a vertical position of the float within the interior of the device body. In addition, a defoaming member is positioned between the first and second movable valve members.

In accordance with another aspect, a bubble trap comprises a device body possessing an interior, a blood inlet port in the device body communicating with the interior of the device body, a blood outlet port in the device body communicating with the interior of the device body, a gas outlet port adapted to be connected to a negative pressure source which withdraws gas under vacuum, a filter member arranged along a first communication path between the interior of the device body and the gas outlet port which permits passage of a gas portion of the bubbles and prevents passage of a blood portion of the bubbles, an opening positioned along a second communication path between the interior of the device body and the gas outlet port that is different from the first communication path, and a movable valve member movable between a closed position in which the movable valve member closes the opening to prevent flow through the opening and an open position to permit flow through the opening. A float is positioned in the interior of the device body and is vertically movable in response to a change of a blood level in the device body associated with a change in an amount of bubbles in the interior of the device body, and at least one arm connects the valve member to the float so that downward movement of the float from a vertically higher position to a vertically lower position due to a change in the blood level in the interior of the device body moves the valve member from the closed position to the open position to permit flow through the opening toward the gas outlet port.

Another aspect involves a method of removing bubbles in an extracorporeal circuit comprising introducing blood from a patient into an interior of a device body, contacting bubbles in the blood with a filter member to break the bubbles into gas and blood, operating a negative-pressure source to draw the gas out of a gas outlet port of the device body along a first communication path which is different from a second communication path provided with an opening that is closed when a level of blood in the interior of the device body is above a predetermined blood level, opening the closed opening when the level of blood in the interior of the device body is below the predetermined blood level and contacting the bubbles in the blood with a defoaming member to break the bubbles into gas and blood, and drawing the gas produced by contact of the bubbles with the defoaming member along the second communication path through operation of the negative-pressure source.

BRIEF DESCRIPTION OF THE DRAWING FIGURES

DETAILED DESCRIPTION

Figure 1:
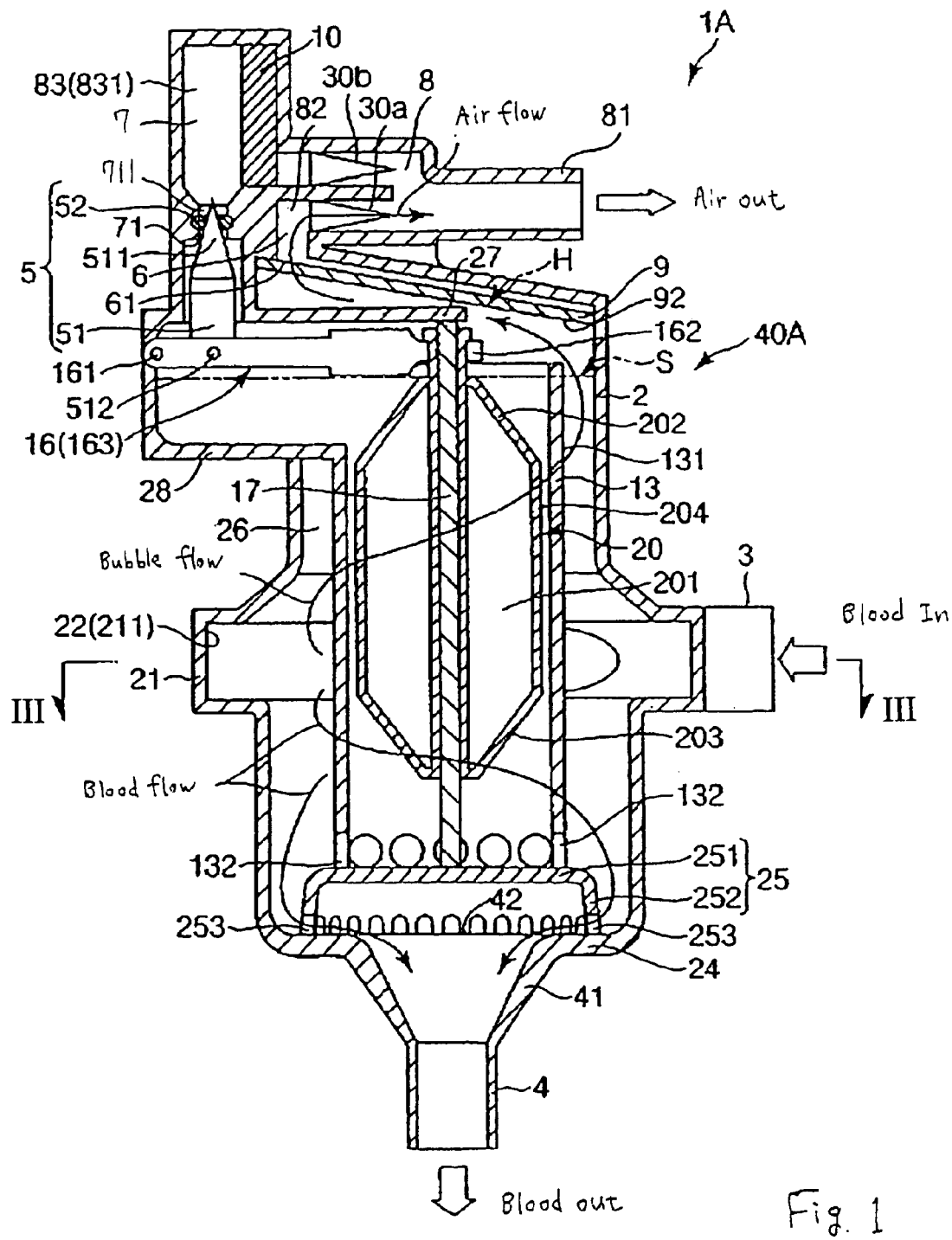
FIG. 1 is a vertical cross-sectional view of a bubble trap according to a first embodiment showing a state in which the second communication passage is closed.
Figure 2:
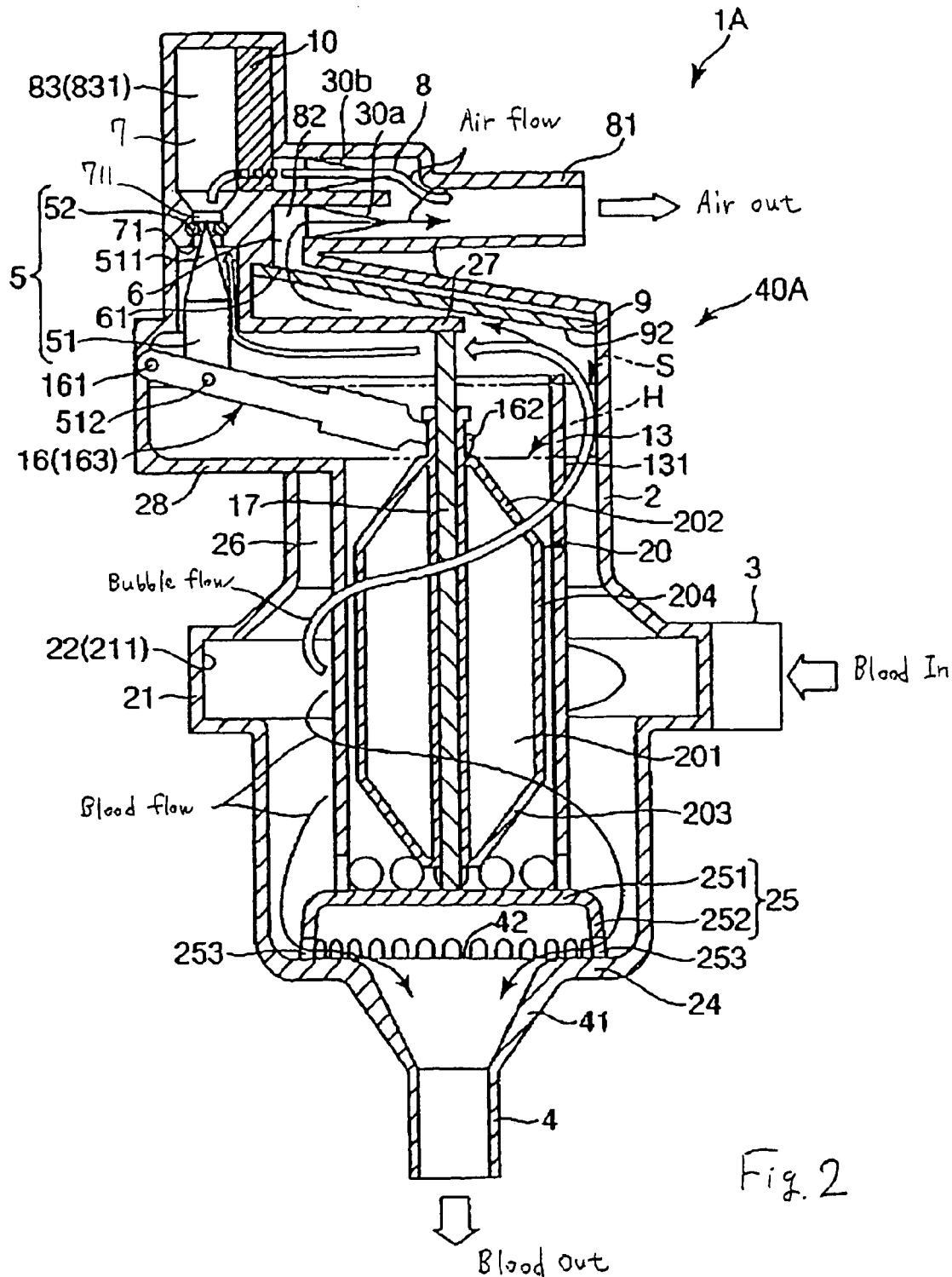
FIG. 2 is a vertical cross-sectional view of the bubble trap showing a state in which the second communication passage is opened.

A first embodiment of a bubble trap disclosed here is shown in FIGS. 1 and 2. FIG. 1 illustrates the bubble trap in a state in which the second communication passage is closed while FIG. 2 shows the bubble trap in a state in which the second communication passage is opened. The bubble trap 1A is configured and adapted to remove bubbles from blood undergoing extracorporeal circulation.

The bubble trap 1A shown in FIGS. 1 and 2 includes a device body 40A through which blood is to flow, a negative-pressure chamber 8 provided in the upper portion of the device body, a defoaming member 10 and check valves 30a, 30b arranged in the negative-pressure chamber 8, first and second communication passages 6, 7 (communicators) that extend between and provide communication between the interior of the device body 40A and a gas outlet port 81 of the negative-pressure chamber 8, a filter member 9, a valve mechanism 5 that opens and closes a gate or opening 711 of the second communication passage 7, a float 20 arranged to vertically move within the device body 40A, and a link mechanism 16 coupling the valve mechanism 5 and the float 20. In the illustrated construction of the bubble trap 1A, the second communication passage 7 at its gate 711 is normally closed (hereinafter referred to as a "closed state") by the action of the valve mechanism 5. However, when bubbles enter the device body 40A together with blood in a certain amount, the second communicator 7 is opened (hereinafter referred to as an "open state").

The material forming the device body 40A and the negative-pressure chamber 8, including the first and second communication passages 6, 7, is not particularly limited, but is preferably a comparatively rigid resin, e.g. polycarbonate, acryl resin, polyethylene terephthalate, polyethylene, polypropylene or polystyrene. The material is preferably substantially transparent so that the interior, e.g., blood condition, can be visually observed.

The device body 40A includes a swirl-flow former (outer shell) 2 in the form of a bottomed cylinder, a partition wall (inner shell) 13 positioned within the swirl-flow former 2, an inlet port 3 through which blood is introduced into the swirl-flow former 2, and an outlet port 4 through which the blood in the swirl-flow former 2 exits to outside the bubble trap 1A.

The swirl-flow former 2 has an interior space in the form of an annular chamber or body (i.e., nearly circular in cross-section) that serves to cause a swirl flow of the blood. During use, the bubble trap 1A is oriented so that the axis (support shaft 17) of the swirl-flow former 2 is positioned vertically.

Figure 3:
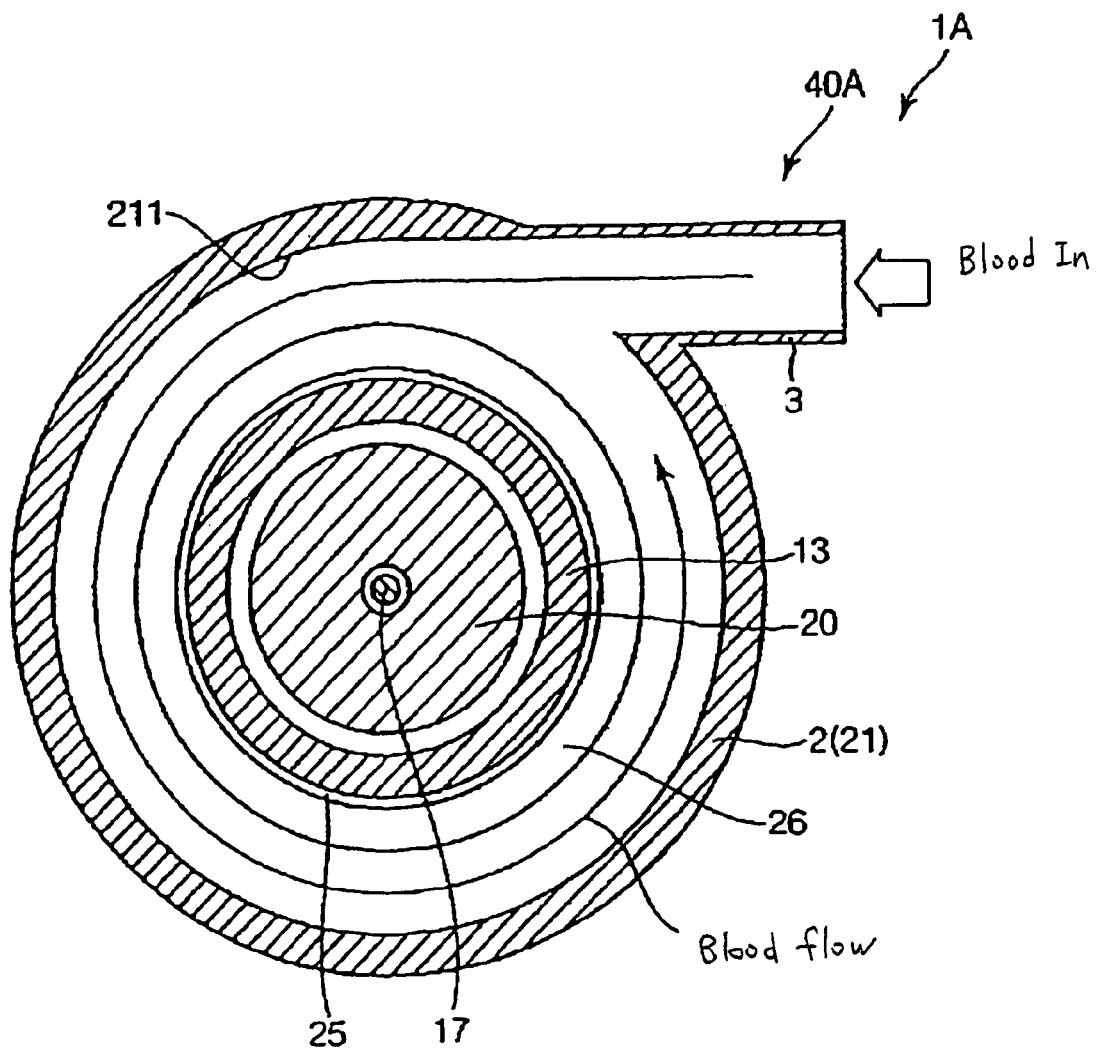
FIG. 3 is a cross-sectional view of the bubble trap taken along the section line III-III in FIG. 2 and FIG. 7.

The intermediate portion of the swirl-flow former 2 (generally the axial central portion of the swirl-flow former 2) includes a diametrical enlargement 21 possessing inner and outer diameters that are enlarged relative to axial ends of the swirl-flow former. The inlet port 3 is provided at the diametrical enlargement 21 and is oriented to extend or protrude nearly tangentially to the inner peripheral surface 211 diametrical enlargement 21 as generally shown in FIG. 3.

The device body 40A is thus constructed to positively cause a swirl flow in the blood entering the swirl-flow former 2 through the inlet port 3.

The outlet port 4 extends or protrudes downwardly from the bottom (lower part) of the swirl-flow former 2. The outlet port 4 includes a boundary 41 with the swirl-flow former 2. The boundary 41 possesses a tapering shape that reduces in diameter in the downward direction to form a funnel (converging) shape. This allows the blood in the swirl-f low former 2 to easily flow toward the outlet port 4.

A lid 25 is provided in the vicinity of the portion of the swirl-flow former 2 above the bottom 24 of the swirl-flow former 2. The lid 25 covers the upper opening 42 of the outlet port 4. The lid 25 comprises a top plate 251 in the form of a disk and a connection portion 252 that connects the top plate 251 to the bottom 24 of the swirl-flow former 2. The connection portion 252 is formed along the entire periphery of the top plate 251. The connection portion 252 is provided with a plurality of openings 253 that extend through the connection portion 252 and are circumferentially spaced apart around the circumference of the connection portion. The blood in the swirl-flow former 2 is able to reach the outlet 4 through the openings 253.

The partition wall 13 is arranged on the top plate 251 of the lid 25. In the illustrated embodiment, the partition wall 13 is cylindrical in form, extending in a spaced manner along the circumference of the inner peripheral surface 22 (inner peripheral wall 211) of the swirl-flow former 2. The partition wall 13 is concentric to the swirl-flow former 2, with a gap (annular-shaped space) 26 being formed between the outer peripheral surface 131 of the partition wall 13 and the inner peripheral surface 22 of the swirl-flow former 2. As shown in FIGS. 1 and 2, a swirl flow takes place in the gap 26 in the device body 40A, whereas there is less occurrence or no occurrence of such swirl flow on the inner side of the partition wall 13.

A plurality of through-holes 132 penetrate the partition wall 13 at positions axially spaced (i.e., in the vertical direction) from the diametrical enlargement 21 (inlet port 3) of the swirl-flow former 2. In the illustrated embodiment, the through-holes 132 are positioned in the lower part of the partition wall 13. The through-holes 132 are spaced apart along the circumference of the partition wall 13. Blood introduced into the swirl-flow former 2 is thus able to flow toward the inner side of the partition wall 13. This maintains the blood, in the gap 26, at a level nearly equal to the blood level on the inner side of the partition wall 13. Therefore, the blood can be kept at an equal level or height H wholly within the device body 40A.

The float 20 is positioned on the inner side of the partition wall 13. The float 20 moves inside the partition wall 13 in response to a change in the level H of the blood within the device body 40A.

The float 20 is circular cylindrical in its outer shape and constructed as a hollow body possessing a hollow space (lumen) 201. This allows the float 20 to be buoyant in the blood within the device body 40A. Though the float 20 is illustrated as a hollow body, the float is not limited in this regard. The float may be constructed as a solid body provided that the float is able to float, or exhibit buoyancy in the blood within the device body 40A.

The upper portion 202 of the float 20 possesses a tapering shape having an outer diameter that decreases toward the upper end. The lower portion 203 of the float 20 also possesses a tapering form having an outer diameter that decreases toward the lower end, nearly similar to the upper portion 202. An intermediate portion 204 of the float between the tapering ends 202, 203 possesses a constant outer diameter. This configuration of the float 20 reduces the float's resistance to the blood when it moves. This thus helps ensure that the float moves in response to a change in the liquid (blood) level H.

As mentioned before, little or no swirl flow occurs with respect to the blood on the inner side of the partition wall 13. By locating the float 20 on the inner side of the partition wall 13, the effect of the swirl flow is not as likely to act on the float 20 so that, for example the float 20 is not as susceptible to being pulled downward by the vortex occurring in the liquid surface. Thus, the float 20 is able to reliably move in response to a change in the liquid level H.

The float 20 rests in its upper limit position in a state in which the device body 40A is wholly filled with blood so that the liquid level over its major part is in contact with the lower surface 92 of the filter member 9. In the state shown in FIG. 2 in which a number of bubbles have entered the device body 40A together with blood so that the liquid level H is at a position lower than that of FIG. 1, the float 20 is lowered (i.e., moves) downwardly from the upper limit position to a position lower than the FIG. 1 position.

The material of which the float 20 is fabricated is not particularly limited, but materials similar to those mentioned above in connection with the device body 40A can be employed, though other materials can also be used.

A support shaft 17 is arranged within the device body 40A. The support shaft 17 passes through the float 20 in the axial or lengthwise direction (i.e., vertically). The support shaft 17 is in the form of a rod having an upper end supported by a bearing 27 projecting from the inner peripheral surface 22 of the device body 40A and a lower end supported by the top plate 251 of the lid 25.

The float 20 moves up and down along the support shaft 17. On the other hand, the support shaft 17 prevents the float 20 from swinging horizontally (moving laterally in the leftward and rightward directions in FIG. 1) due to swirling flow. The support shaft 17 thus functions as a position-keeping or position-maintaining means that maintains the float 20 in position.

The support shaft 17 may be formed integral with the device body 40A, or can be constructed separate from the device body 40A and then joined to the device body 40A.

The negative-pressure chamber 8 has a first communication passage 6, a second communication passage 7, and a gas outlet port 81. The first and second communication passages 6 provide different paths of communication between the gas outlet port 81 and the interior of the device body 40A. The negative-pressure chamber 8 is comprised of two chambers, a first chamber 82 and a second chamber 83. As mentioned above, the negative-pressure chamber 8 is provided in the upper part of the device body 40. The gas outlet port 81 of the negative-pressure chamber is in communication with the interior of the device body 40A by virtue of the first and second communication passages 6, 7. In the illustrated embodiment, the negative-pressure chamber 8 is at the upper part of the device body 40A by virtue of the negative-pressure chamber 8 being formed integral with and as a part of the device body 40A. Other constructions are, of course possible, for providing the negative-pressure chamber 8 at an upper part of the device body 40A.

The gas outlet port 81 is connected to a gas-evacuation means that draws a gas under vacuum. The gas-evacuation means can be a suitable type of evacuator for drawing a vacuum. An example of a gas-evacuation means is an on-wall vacuum source at the operating room. The on-wall vacuum refers to the vacuum (evacuation) piping set that is typically located on the wall in a surgical operation room. Though operation of such gas-evacuation means, the negative-pressure chamber 8 can be kept at negative pressure. Due to this, when bubbles come into the device body 40A together with blood, the bubbles move into the negative-pressure chamber 8 by way of the first communication passage 6 and the open gate 711 (in the state shown in FIG. 2) of the second communication passage 7, thus being allowed to exit (evacuated) out of the negative-pressure chamber 8. This is generally represented by "bubble flow" arrow in FIGS. 1 and 2. The magnitude of negative pressure in the negative-pressure chamber 8 is not particularly limited, but is preferably 250-350 mmHg, for example.

The check valves 30a, 30b are respectively arranged in the first and second chambers 82, 83, in positions closer to the gas outlet port 81 (i.e., on the downstream side). The check valve 30a positively prevents the gas of the first chamber 82, being drawn by the gas-evacuation means, from flowing reverse to the first communication passage 6 or into the second chamber 83. This helps positively remove the gas out of the gas removal device 1A. Similar operational characteristics apply to the check valve 30b.

In the illustrated embodiment, both of the check valves 30a, 30b are in the form of a duckbill valve. However, the check valves 30a, 30b are not limited in this respect and may be any type of a valve which permits the gas to flow only toward the gas-evacuation means.

The defoaming member 10 is arranged in the second chamber 83. The defoaming member 10 carries an antifoaming agent and is arranged nearby the gate 711 of the second communication passage 7 (i.e., upstream of the check valve 30b). This forms a small space 831 between the deforming member 10 and the gate 711 of the second communication passage 7. Bubbles entering through the opened gate 711 of the second communication passage 7 are temporarily stored in the small space 831. If the second chamber 83 (negative-pressure chamber 8) is formed of a substantially transparent material, the presence of bubbles in the small space 831 can be visually confirmed.

The antifoaming agent, carried in the defoaming member 10, serves to break the bubbles when the bubbles contact the defoaming member. An example of a typical antifoaming agent is silicone. By virtue of the defoaming member 10, bubbles stored in the small space 831 are positively broken by the antifoaming agent carried in the deforming member 10 through contact therewith. When the bubbles are broken, the blood on the outer periphery of the bubbles is not allowed to pass through the defoaming member 10, and thus is not allowed to pass through the check valve 30b. Instead, only the air (gas) forming the bubbles is allowed to pass through the defoaming member 10 and the check valve 30b. This permits the blood to go back to the device body 40A, thus removing only air out of the bubble trap 1A. As a result, the blood is not needlessly spent.

The antifoaming agent is carried by or applied to the defoaming member 10 by, for example, impregnating, applying or spraying a material with a solution containing an antifoaming agent, followed by drying. The material forming the defoaming member 10 is preferably a cellular material, for example foamed polyurethane.

The first communication passage 6a includes a lower opening (first body-side opening) 61, while the second communication passage 7 includes a lower opening (second body-side opening) 71. The lower opening 61 of the first communication passage 6 and the lower opening 71 of second communication passage 7 are located below the negative-pressure chamber 8, but in the upper part of the device body 40A.

The filter member 9 is positioned in a manner covering the lower opening 61 of the first communication passage or communication passage 6. The filter member 9 is thus positioned between the interior of the device body 40A and the negative-pressure chamber 8. The filter member 9 is a liquid-repellant film member formed to permit the passage of the gas portion of bubbles within the device body 40A without allowing the passage of the blood portion of bubbles within the device body 40A. The filter member 9 is preferably hydrophobized at its surface or made by a hydrophobic film.

An example of the material for the hydrophobic film includes polytetrafluoro-ethylene (PTFE).

When bubbles come into the device body 40A together with blood, the bubbles rise in the device body 40A and the gas in the bubbles pass through the filter member 9 into the negative-pressure chamber 8 where it exits to the outside of the bubble trap 1A through the gas outlet port 81 of the negative-pressure chamber 8. The filter member 9 prevents blood from passing but allows gas (air) in the bubbles to pass into the negative-pressure chamber 8. That is, when the bubbles contact the filter member 9, the bubbles are broken and separated into blood (i.e., blood on the outer periphery of the bubble) and gas (i.e., air contained in the bubble), with the gas being able to pass through the filter member 9 while the blood is prevented from passing through the filter member 9.

The filter member 9 is inclined relative to a horizontal plane. This allows the bubbles, rising in the device body 40A, to move along the inclination (lower surface 92) of the filter member 9 and toward one side (toward the left in FIGS. 1 and 2) of the device body 40A (i.e., toward the lower opening 61 of the first communication passage 6). This makes it possible to collect the bubbles with further smoothness and swiftness.

A box-like receiver part 28 is formed in the device body 40A (swirl-flow former 2) at a position below the gate 711 of the second communication passage 7. A part of the valve mechanism 5 that opens and closes the gate 711 of the second communication passage 7 and a part of the link mechanism 16 that couples the valve mechanism 5 and the float 20 are positioned in the receiver part 28.

The valve mechanism 5 comprises a resilient member 52 arranged in the inner periphery of the gate 711 of the second communication passage 7 and a movable valve member 51. In the illustrated embodiment, the movable valve member is in the form of a needle member.

The needle member 51 and the float 20 are placed at different locations horizontally (i.e., they are spaced apart in the horizontal direction). Consequently, the link mechanism 16 has an arm 163 coupling the needle member 51 and the float 20.

The needle member 51 has an apex 511 possessing a nearly conical (or pyramidal) form. The resilient member 52 is in the form of a ring extending along the circumference of the inner periphery of the second communication passage 7. By way of the needle member 51 and the resilient member 52, the gate 711 of the second communication passage 7 can be closed by placing the outer peripheral surface of the apex 511 into close contact with the resilient member 52 as shown in FIG. 1. The closed gate 711 of the second communication passage 7 can be opened by moving the outer peripheral surface of the apex 511 away from the resilient member 52 as shown in FIG. 2.

The valve mechanism 5 is thus able to open and close the gate or opening 711 of the second communication passage 7 based upon the operation of the valve mechanism.

The arm 163 has one end 161 rotatably supported by the receiver part 28 and the other end 162 coupled to the float 20. The arm 163 also has an intermediate portion rotatably supporting the lower portion 512 of the needle member 51. When the float 20 moves vertically in response to a change in the liquid level H, the arm 163 rotates about the one end 161. By virtue of the rotation of the arm 163, the needle member 5 moves vertically toward and away from the resilient member 52, i.e., the valve mechanism 5 opens and closes the gate 711 of the second communication passage 7.

When the liquid level H (float 20 position) rises to a level exceeding a reference position S, the needle member 51 rises into contact with the resilient member 52 due to the rising float 20. This closes the gate or opening 711 of the second communication passage 7. On the other hand, when the liquid level H is lowered to the reference position S or lower, the needle member 51 moves downwardly away from the resilient member 52 due to the lowering of the float 20. This opens the gate or opening 711 of the second communication passage 7.

Thus, in the bubble trap 1A, when bubbles come into the device body 40A together with blood, the liquid level H changes in accordance with the influx rate of bubbles. In the (usual) state in which there are incoming bubbles in an amount that the liquid level H is not at the first position S or lower, the gate 711 of the second communication passage 7 is closed, i.e., is in the state shown in FIG. 1, as noted before. In the FIG. 1 state, the bubbles (i.e., the gas in the bubbles) pass through the filter member 9 and the first communication passage 6 in that order to enter the first chamber 82 of the negative-pressure chamber 8. The bubbles which have entered the first chamber 82 are allowed to pass through the check valve 30a and exit through the gas outlet port 81.

On the other hand, in the state in which there are incoming bubbles in an amount causing the liquid level H to be lowered to the reference position S or lower (in the state in which a number of bubbles are flowing in), the gate or opening 711 of the second communication passage 7 is opened, i.e., is in the state shown in FIG. 2, as noted before. In the FIG. 2 state, the bubbles within the device body 40A include those moving toward the first communication passage 6 similar to the FIG. 1 state and those moving toward the gate 711 of the second communication passage 7. Because the opened gate 711 of the second communication passage 7 provides an easier path for the bubbles to pass through than the first communication passage 6 covered by the filter member 9, the majority of bubbles in the device body 40A preferably passes through the opened gate 711 of the second communication passage 7 rather than through the first communication passage 6. The bubbles, passing through the opened gate 711 of the second communication passage 7 flow into the second chamber 83 and then pass through the check valve 30b, thus exiting through the gas outlet port 81. Meanwhile, the bubbles passing through the first communication passage 6 exit through the gas outlet port 81.

With this structure, the bubble trap 1A is allowed to remove bubbles from blood undergoing extracorporeal circulation irrespective of the influx rate of bubbles into the bubble trap 1A. This can help positively suppress the blood from activating (being damaged) due to the contact with bubbles. In addition, bubbles are not supplied to the oxygenator and hence to the patient.

The lower portion 512 (coupled to the arm 163) of the needle member 51 is located closer to the one end 161 of the arm 163 than the other end 162. That is, the lower portion 512 of the needle member 51 is located closer to the end of the arm 163 that is connected to the receiver part 28 than to the end of the arm 163 that is connected to the float 20 as shown in FIGS. 1 and 2. Accordingly, the needle member 51 has a vertical stroke (hereinafter, referred to as "needle member travel") smaller relative to the vertical stroke of the float 20 (hereinafter, referred to as "float travel"). The ratio of the needle member travel to the float travel is given by the ratio of the distance between the one end 161 and the lower portion 512 to the distance between the one end 161 and the other end 162. The ratio of the needle member travel to the float travel (i.e., (needle travel)/(float travel)), is not particularly limited. By way of example, though, the ratio of the needle member travel to the float travel is preferably in a range of 0.1-1.0, more preferably a range of 0.2-0.3.

The needle member travel is in proportion to the float travel, i.e., the influx rate of bubbles. In the valve mechanism 5, as the influx rate of bubbles increases, the needle member travel increases to increase the spacing between the needle 51 and the resilient member 52, i.e., increasing the opening degree of the valve.

In the case a number of bubbles entering, the valve opening degree increases so that the bubbles can easily pass through the gate 711 of the second communication passage 7. This accordingly removes bubbles out of the bubble removal device 1A with higher efficiency and further positiveness.

The material forming the needle member 51 and the arm 163 is not especially limited, but can be the materials mentioned above in connection with the device body 40A.

The material forming the resilient member 52 is also not particularly limited, though natural rubber or synthetic rubber are examples. Also, the material of the resilient member 52 can also be used as the material for forming the needle 51.

Where the needle member 51 is made of a resilient material, the resilient member 52 may be formed of a material higher in rigidity than the needle member 51 (e.g., the materials mentioned in connection with the device body 40A).

Figure 6:
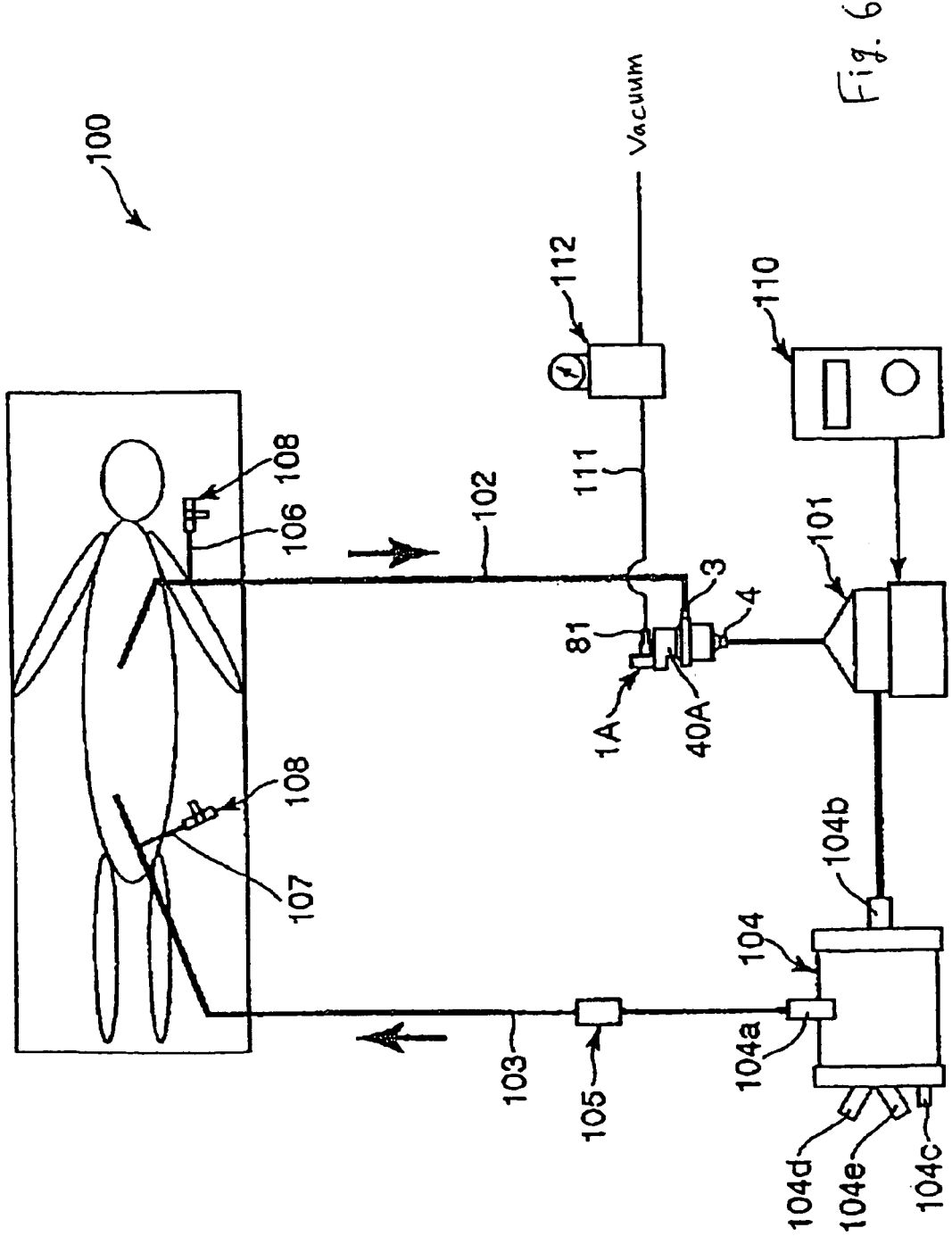
FIG. 6 is a schematic illustration of an embodiment of an extracorporeal apparatus using the bubble trap disclosed herein.

FIG. 6 illustrates an example of an extracorporeal apparatus 100 employing the bubble trap 1A. The extracorporeal apparatus 100 includes a centrifugal pump (blood pump) 101 for feeding blood, a venous line 102 connecting between a suction port of the centrifugal pump 101 and a patient, an arterial line 103 connecting between a delivery port of the centrifugal pump 101 and the patient, a bubble trap 1A set up on the venous line 102, an oxygenator 104 set up on the arterial line 103 to perform gas exchange with blood, a flow meter 105 set up on the arterial line 103, and a control unit 110 controlling operation (rotational speed) of the centrifugal pump 101.

In the extracorporeal apparatus 100, the blood passes through the venous line 102, the bubble trap 1A, the centrifugal pump 101, the oxygenator 104, the arterial line 103 and the flow meter 105, and is then returned to the patient. That is, in the extracorporeal apparatus 100, the blood flows in the direction of the arrows in FIG. 6.

The oxygenator 104 includes a blood inlet port (inlet port) 104b through which blood flows into the oxygenator 104, a blood outlet port (outlet port) 104a through which blood flows from the oxygenator 104, a gas inlet port 104c, a gas outlet port (not shown), a heating-medium inlet port 104d and a heating-medium outlet port 104e. The interior of the oxygenator 104 receives a hollow fiber membrane bundle comprised of a multiplicity of integrated hollow fiber membranes having a gas-exchange function, and a filter member arranged around the hollow fiber membrane bundle to capture bubbles.

The gas outlet port 81 of the bubble trap 1A is connected to an on-wall vacuum (gas-evacuation means) through an evacuation line 111. On the evacuation line 111, a negative-pressure regulator 112 is provided to regulate the pressure in the negative-pressure chamber 8.

When the centrifugal pump 101 operates, the blood drawn from the patient through a catheter (not shown) passes through the venous line 102 and then enters the inlet port 3 of the bubble removal device 1A. In the bubble trap 1A, during the usual state in which the amount of incoming bubbles causes the liquid (blood) level H to not be at a reference level S or lower, the gate 711 of the second communication passage 7 is closed so that the bubbles are removed through the filter 9. The blood, removed of bubbles, exits the outlet port 4 of the bubble trap 1A and passes through the centrifugal pump 101, thus being sent to the oxygenator 104. In the oxygenator 104, gas exchange (addition of oxygen, removal of carbon dioxide) is carried out for the blood. The gas-exchanged blood which has passed through the oxygenator 104 flows through the arterial line 103 and is sent back to the patient through the catheter.

On the other hand, in the state where the number of bubbles flowing into the bubble trap 1A is of such an amount that the liquid level H drops to a reference level S or lower, the gate 711 of the second communication passage 7 is open so that the bubbles are removed from the blood in the manner previously described.

In this manner, bubbles in blood can be removed in the bubble trap 1A with efficiency and positiveness irrespective of the influx rate of bubbles to the bubble trap 1A. Thus, the bubbles are thus not likely to be sent to the oxygenator and hence to the patient. In addition, in the bubble trap 1A, the blood can be suppressed (reduced) from activating (being damaged) due to the contact thereof with the bubbles. As a result, in the extracorporeal apparatus 100, the blood circulating through the extracorporeal apparatus 100 can be suppressed from being damaged.

As mentioned before, the negative-pressure chamber 8 is connected to the gas-evacuation means and kept at and drawn under negative pressure. In the extracorporeal apparatus 100, the negative-pressure chamber 8 is preferably applied with suction pressure at all times.

Figure 4:
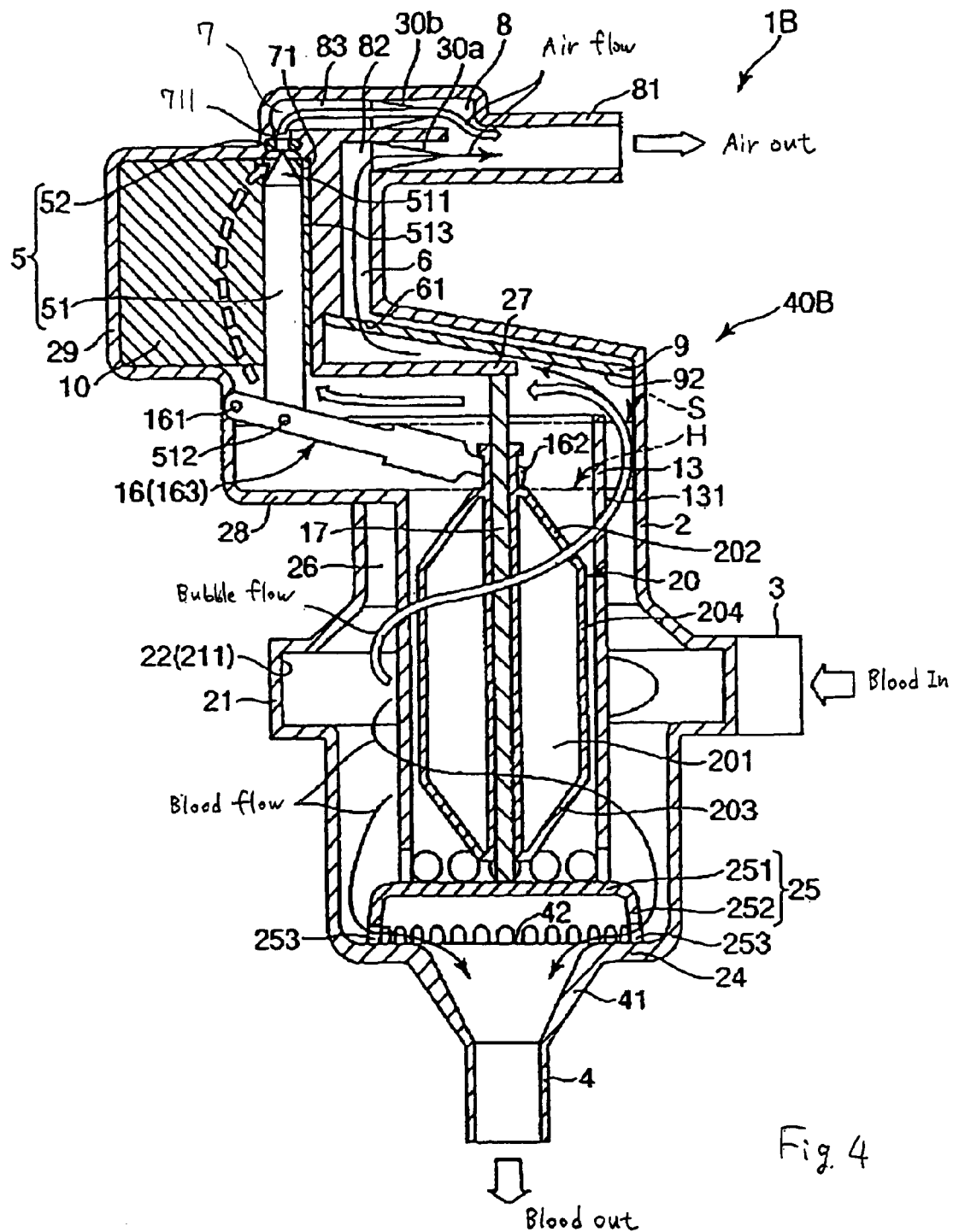
FIG. 4 is a vertical cross-sectional view of a bubble trap according to a second embodiment showing a state in which the second communication passage is open.

FIG. 4 illustrates a second embodiment of the bubble trap in which the bubble trap is in the state in which the second communication passage is open. The following description primarily describes differences between this embodiment and the embodiment described above. A detailed description of features in the second embodiment that are similar to those in the first embodiment is not repeated once again.

This second embodiment is similar to the first embodiment, except that the location of the defoaming member differs.

The device body 40B of the bubble trap 1B shown in FIG. 4 includes a defoaming-member receiving part 29 that accommodates a defoaming member 10. The defoaming-member receiving part 29 is located nearby the lower opening 71 for the gate 711 of the second communication passage 7.

A defoaming member 10 is received in the defoaming-member receiving part 29. The defoaming member 10 is arranged in contact with the needle member 51 at its outer periphery 513. The needle member 51 is thus arranged so that it passes through the defoaming member 10.

In the bubble trap 1B, the bubbles moving up in the device body pass through the defoaming member 10 while contacting the defoaming member 10 before passing through the opened gate 711 of the second communication passage 7. The bubbles contacting the defoaming member 10 are broken and so only the air of the bubbles is able to pass through the opened gate 711 of the second communication passage 7.

This structure provides an advantage in that the blood on the outer periphery of bubbles, when the bubbles are broken, is prevented from passing to the gas exit port 81 and to the gas-evacuation means downstream of the gas exit port 81.

Figure 5:
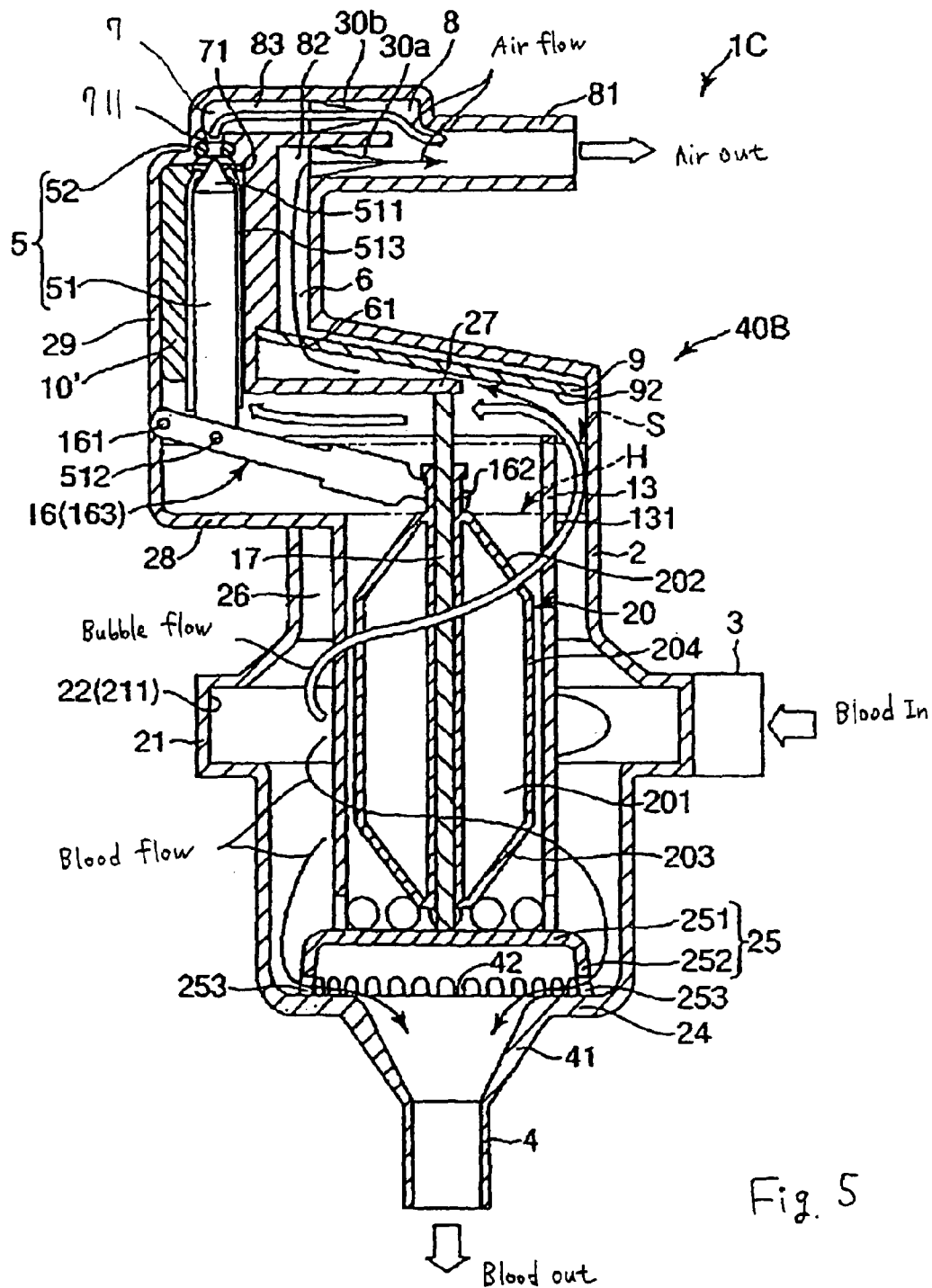
FIG. 5 is a vertical cross-sectional view of a bubble trap according to a third embodiment showing a state in which the second communication passage is open.

FIG. 5 illustrates a third embodiment of the bubble trap in which the bubble trap is in the state in which the second communication passage is open. The following description primarily describes differences between this embodiment and the embodiments described above. A detailed description of features in the third embodiment that are similar to those in the embodiments described above is not repeated once again.

This embodiment is similar to the second embodiment, except that the shape (size) of the defoaming member is different.

The bubble trap 1C shown in FIG. 5 has a defoaming member 10' which is smaller in size than the defoaming member 10 described in the second embodiment. This reduces the overall size of the bubble trap 1C so that it is smaller than the bubble trap 1B described in the second embodiment. In the bubble trap 1C constructed in this way, there are possible cases in which the bubbles moving up in the device body 40 in the major part thereof pass through between the defoaming member 10' and the outer periphery 513 of the needle member 51 while contacting the defoaming member 10'. In this case, the air (bubble) is suppressed in the resistance against the foaming member 10' when passing through the defoaming member 10'. Hence, the air is able to reach the gate 711 of the second communication passage 7 swiftly.

Figure 7:
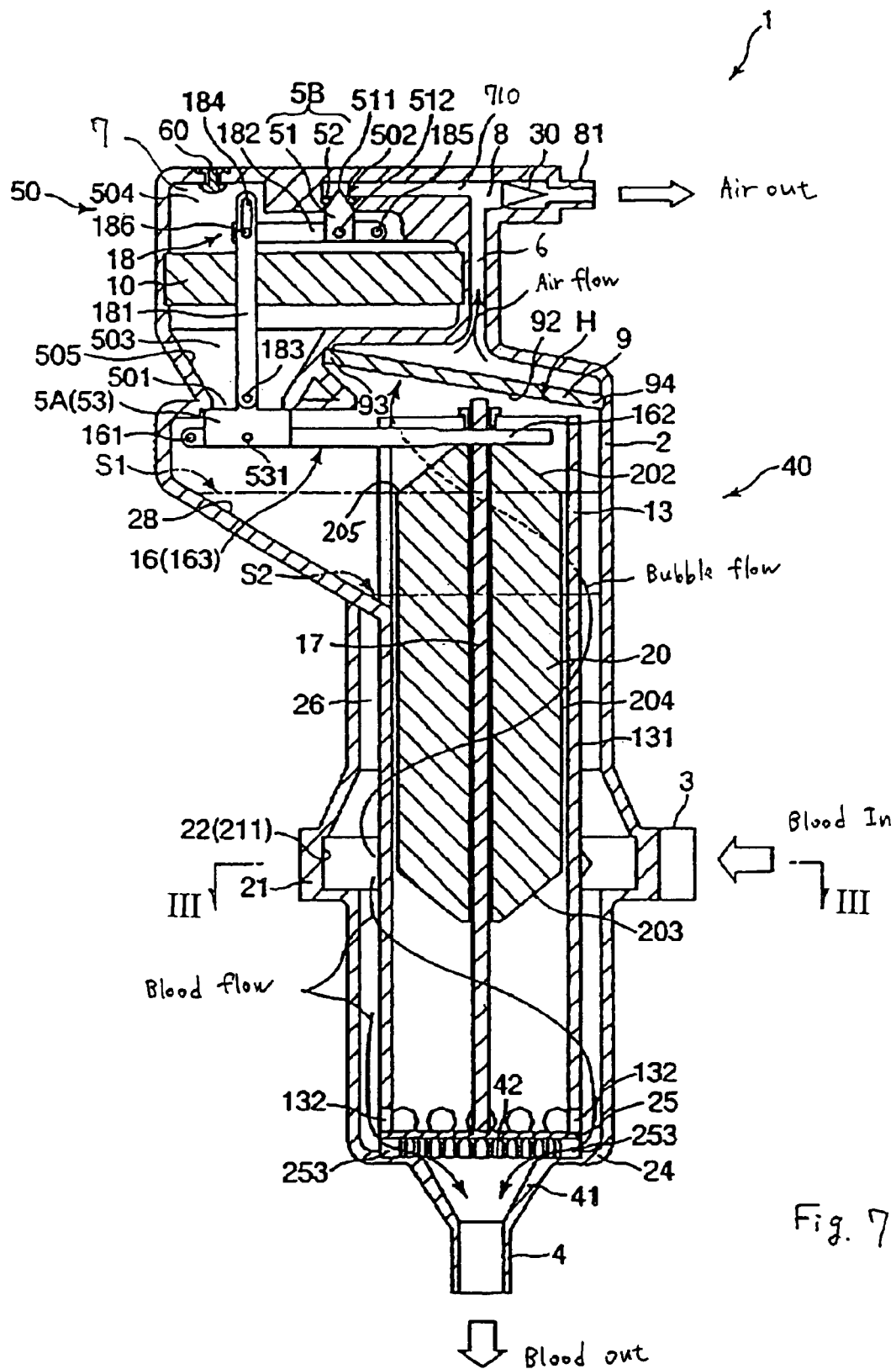
FIG. 7 is a vertical cross-sectional view of a bubble trap according to another embodiment.
Figure 8:
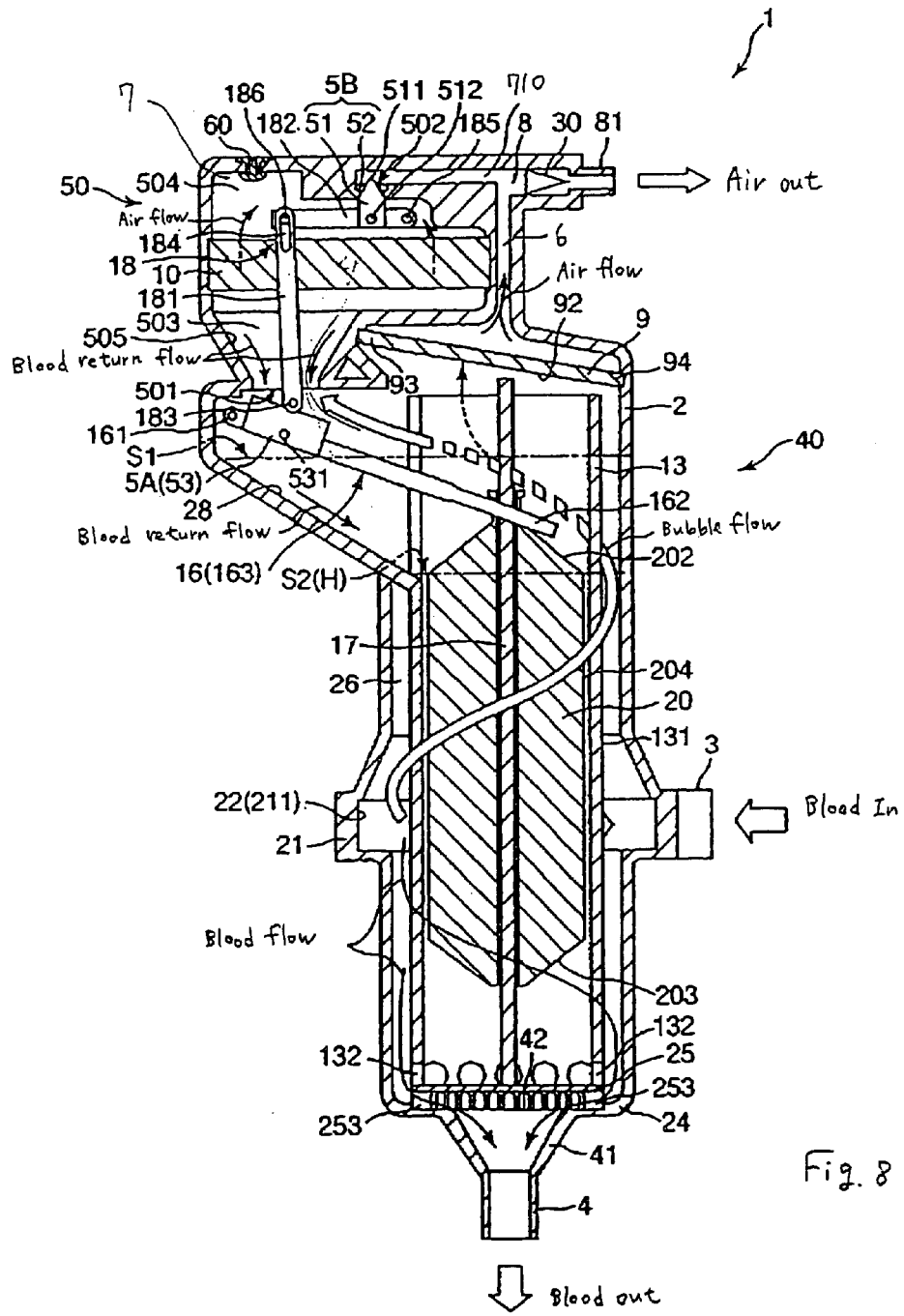
FIG. 8 is a vertical cross-sectional view of the bubble trap shown in FIG. 7 in a different state.
Figure 9:
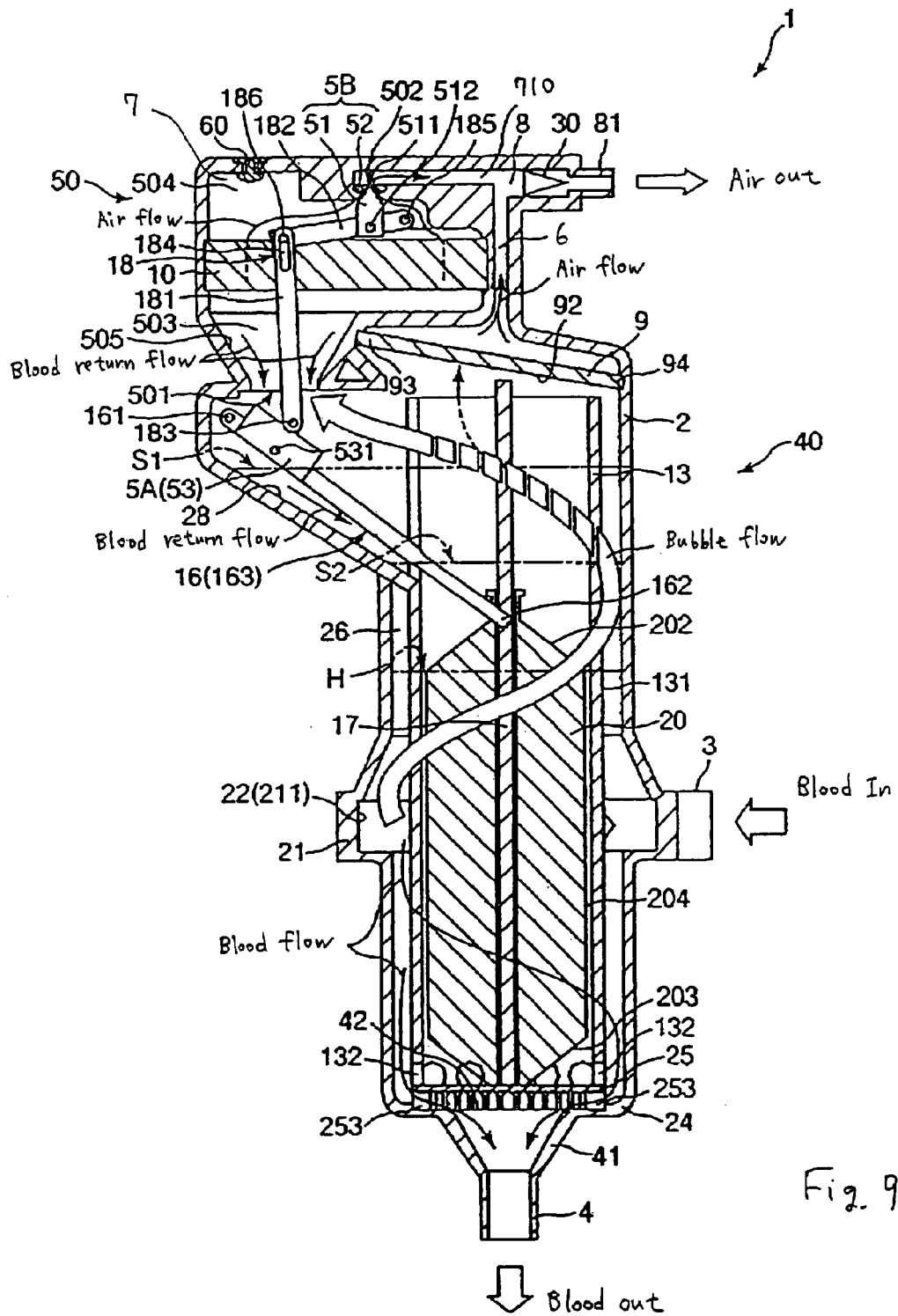
FIG. 9 is a vertical cross-sectional view of the bubble trap shown in FIG. 7 in a still different state.

A further embodiment of the bubble trap 1 is shown in FIGS. 7-9. The bubble trap 1 here includes a device body 40 through which blood flows, a negative-pressure chamber 8 positioned at an upper part of the device body 40, a filter member 9 positioned between the negative-pressure chamber 8 and an upper portion of the device body 40, a bubble breaking chamber (defoaming chamber) 50 provided above the device body 40 and adjacent to the negative-pressure chamber 8, a float 20 arranged to move up and down (vertically) within the device body 40, first and second valve mechanisms 5A, 5B operable in accordance with the vertical movement of the float 20, a first link mechanism 16 connecting the float 20 and the first valve mechanism 5A, and a second link mechanism (link mechanism) 18 connecting the first valve mechanism 5A and the second valve mechanism 5B. In the illustrated embodiment, the negative-pressure chamber 8 is at the upper part of the device body 40 by virtue of the negative-pressure chamber 8 being formed integral with and as a part of the device body 40. Other constructions are, of course possible, for providing the negative-pressure chamber 8 at the upper part of the device body 40A.

As shown in FIGS. 7-9, the bubble trap 1 is adapted to take three different forms or states in accordance with the vertical position of the float 20. In the state shown in FIG. 7 (first state), the first and second valve mechanisms 5A, 5B (first and second gates 501, 502) are both closed. In the state shown in FIG. 8 (second state), the first valve mechanism 5A is opened while the second valve mechanism 5B is closed. In the state shown in FIG. 9 (third state), the first and second valve mechanisms 5A, 5B are both open. The bubble trap 1 is usually or normally in the first state. However, in situations in which a number of bubbles flow into the device body 40 together with blood, the device switches from the first state into the second state or from the first state into the third state through the second state, in accordance with the influx rate of bubbles.

The device body 40, the negative-pressure chamber 8 and the bubble-breaking chamber 50 may be formed integrally together in one piece as in the illustrated embodiment, or may be constructed as separate pieces connected together.

In the state shown in FIG. 7, the float 20 is located in an upper limit position of a movement range of the float. In this state, the device body 40 is filled nearly fully with blood so that the liquid level in the major part is in contact with the lower surface 92 of the filter member 9. In the state shown FIG. 8 in which a comparatively greater number of bubbles flow into the device body 40 together with blood so that the liquid level H is at a position lower than that of FIG. 7, the float 20 descends from the upper limit position down to a position (intermediate position) lower than that of FIG. 7. In the state shown FIG. 9 in which a greater number of bubbles than that of FIG. 8 flow into the device body 40 together with blood so that the liquid level H is at a position further lower than that of FIG. 8, the float 20 further descends from the position shown in FIG. 8.

The negative-pressure chamber 8 is in the upper part of the device body 40 and communicates with the device body 40 through the filter member 9. In this illustrated embodiment, the negative-pressure chamber 8 is formed integrally in one piece with the device body 40. The negative-pressure chamber 8 has a first communication passage 6 (first communicator) through which the gas passing through the filter member 9 flows, a second communication passage 7 (second communicator), a part of which is formed or structured by the bubble breaking chamber 50, and a gas outlet port 81. The first and second communication passages 6, 7 extend between and provide communication between the interior of the device body 40 and the gas outlet port 81 along two separate communication paths. The first and second valve mechanisms are positioned in the second communication passage 7 that provides communication between the interior of the device body 40 and the gas outlet port 81.

A check valve 30 is arranged in the vicinity of a confluence between the first communication passage 6 and the second communication passage 7.

When bubbles flow in the device body 40 together with blood, the bubbles move up in the device body 40 and then pass through the filter member 9. At this time, the bubbles are broken and separated into blood (i.e., blood on the outer periphery of the bubble) and gas (i.e., air contained in the bubble). The gas is drawn into the negative-pressure chamber 8 and then allowed to exit to the outside of the bubble trap 1 through the gas outlet port 81. The blood is not able to pass through the filter member 9 and is sent back to the device body 40.

The bubble-breaking chamber 50 is positioned in the upper part of the device body 40 and is positioned adjacent to the negative-pressure chamber 8. The bubble-breaking chamber 50 is adapted to break (antifoam) the bubbles, which have mingled in the bubble-breaking chamber 50 from the device body 40, and to separate the bubbles into the blood making up the outer periphery of the bubbles and the gas existing in the bubbles. By making the bubble-breaking chamber 50 of a substantially transparent material, it is possible to visually confirm the existence of bubbles in the bubble-breaking chamber 50.

A defoaming member 10 is arranged in the bubble-breaking chamber 50. This divides the bubble-breaking chamber 50 into a first chamber 503 and a second chamber 504, with the second chamber located above the first chamber 503.

An antifoaming agent is carried in the defoaming member 10 which is arranged in a manner separating the first and second chambers 503, 504.

The antifoaming agent, carried in the defoaming member 10, serves to break bubbles when they are contacted with the antifoaming agent. It is typically formed of silicone. By virtue of the defoaming member 10, the bubbles in the bubble-breaking chamber 50 contact the antifoaming agent carried in the defoaming member 10, thus being positively broken. When the bubbles are broken, the blood on the outer periphery of the bubbles is sent back to the first chamber 503 while the gas of the bubbles is sent toward the second chamber 504.

The first chamber 503 has a first gate 501 that opens downward, i.e., toward the device body 40. This places the first chamber 503 in communication with the device body 40.

As shown in FIGS. 8 and 9, when bubbles flow in the device body 40 together with blood with the bubble trap in the second or third state, the bubbles move into the first chamber 503 through the first gate 501. The bubbles move up into contact with the defoaming member 10 where they are separated into blood and gas. The blood is sent back to the first chamber 503, and then to the device body 40 by way of the first gate 501.

The first chamber 503 has an inner periphery (inner peripheral surface) assuming a convergent form, i.e., having a convergent part 505 which possesses an inner diameter gradually decreasing downward. This helps ensure that the blood, returned in the first chamber 503, flows toward the device body 40. Thus, the blood positively flows to (returns to) the device body 40 through the first gate 501.

A slant or inclined surface 28 is positioned in the lower vicinity of the first gate 501. In the illustrated embodiment, this slant surface 28 is arranged formed as the device body 40. The slant surface 28 is inclined so as to extend downwardly and toward the support shaft 17 (i.e., toward the axis of the swirl-flow former 2). In the second and third states, the blood passing through the first gate 501 flows down along the slant surface 28 and returns to the swirl-flow former 2.

The first gate 501 is located lower than the topmost end 93 of the filter member 9. By virtue of this arrangement, when the bubble trap is changed from the states shown in FIGS. 8 and 9 to the state shown in FIG. 7 by the closure of the first gate 501, air remains above the first position S1. However, because the air can be removed by or through the filter member 9, the contact between blood and air can be eliminated relatively swiftly.

The first gate 501 is located nearly equal in height to the lowest end 94 of the filter member 9.

The second chamber 504 has a second gate 502 that opens upward, i.e., toward a passage 710 for the negative-pressure chamber 8. This places the second chamber 504 in communication with the negative-pressure chamber 8.

As shown in FIGS. 8 and 9, when bubbles flow into the device body 40 together with blood in the second or third state of the bubble trap, the bubbles moves into the first chamber 503 through the first gate 501. As mentioned before, the bubbles move up into contact with the defoaming member 10 where they are broken and separated into blood and gas. In the second state of the bubble trap shown in FIG. 8, this gas is stored in the second chamber 504. However, in the third state of the bubble trap, this gas passes through the second chamber 504 and enters the negative-pressure chamber 8 by way of the second gate 502. When the gas enters the negative-pressure chamber, i.e., in the third state, the gas is positively removed from the bubble trap 1 as indicated by the arrow designated "bubble flow" in FIG. 9.

In this manner, when bubbles flow into the device body 40 together with blood, the bubbles break to result in blood and air (gas). The blood is positively sent back into the device body 40, thus preventing the loss (waste) of blood. Meanwhile, because the air is stored in the second chamber 504 or removed through the negative-pressure chamber 8, the blood in the device body 40 is positively inhibited or prevented from contacting the gas. This helps prevent the blood from being damaged or otherwise adversely affected due to contact with gas (air). In addition, bubbles are not likely to be supplied to the oxygenator and hence to the patient.

In the bubble trap 1, the first chamber 503, the defoaming member 10 and the second chamber 504 are arranged in this order, with the first chamber 503 being at the vertically lowest position relative to the defoaming member 10 and the first chamber 503.

With this arrangement, the bubbles (gas) are allowed to move upward relatively easily. At the same time, when the bubbles become broken and are separated into blood and gas, the blood separated from the gas can move downwardly relatively easily. The blood is thus positively sent back to the device body 40, and the gas is prevented from contacting with the blood.

There is also an advantage in that, in the case of bubbles entering the device body successively, the bubbles flow into the bubble-breaking chamber 50 through the first gate 501 and, simultaneously, the blood separated by the defoaming member 10 is returned into the device body 40.

The first gate 501 possesses an opening area greater than the opening area of the second gate 502. This positively places the first valve mechanism 5A open when in the state shown in FIG. 8, and the first and second valve mechanisms 5A, 5B both open when in the state shown in FIG. 9, i.e., in the state in which bubbles flow greater in amount than in the FIG. 8 state. By making the second gate 502 smaller in its opening area, the first gate 501 can be opened in the state shown in FIG. 8 while the second gate 502 is positively closed.

The opening area of the first gate 501 is not particularly limited. By way of example, the opening area of the first gate 501 is preferably 70-400 mm$^2$, more preferably 150-300 mm$^2$.

The opening area of the second gate 502 is also not particularly limited. By way of example, the opening area of the first gate 501 is preferably 3-20 mm$^2$, more preferably 5-12 mm$^2$.

Figure 10:
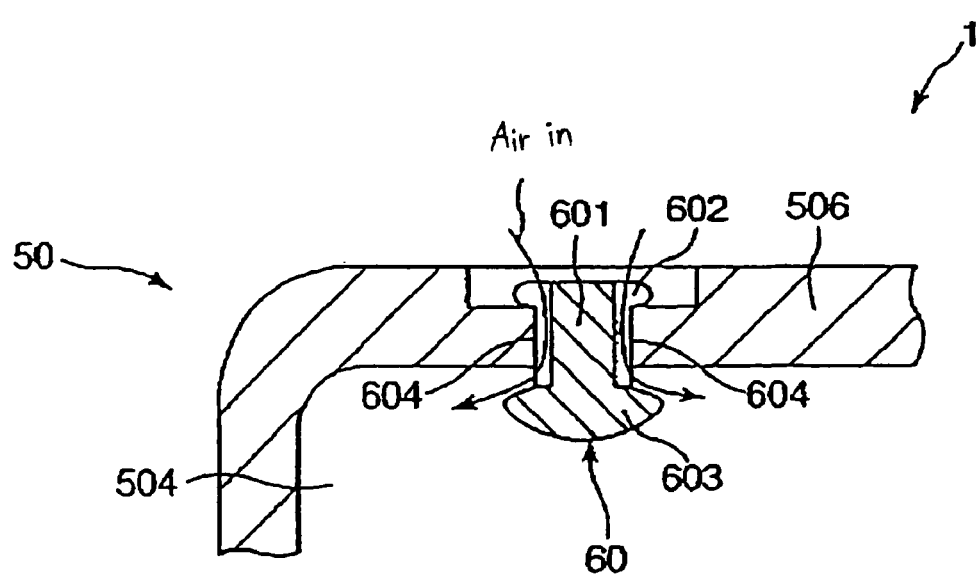
FIG. 10 is an enlarged cross-sectional view of a pressure regulation valve (pressure regulating means) used in the bubble shown in FIGS. 7-9.

As shown in FIGS. 7-9, and in more detail in FIG. 10, a pressure regulation valve (pressure regulating means) 60 is arranged in the upper part (top plate or top wall) of the bubble-breaking chamber 50 (second chamber 504) for regulating pressure. The pressure regulation valve 60 operates to adjust (moderate) the pressure within the bubble-breaking chamber 50 (first and second chambers 503, 504).

The pressure regulation valve 60 is formed of a resilient material and includes a base 601 possessing a circular cylindrical form, an upper flange 602 at the upper end of the base 601, and a lower flange 603 at the lower end of the base 601.

A plurality of grooves 604 are formed in the outer periphery of the base 601. These grooves 604 extend along the lengthwise direction of the valve 60 and are spaced apart along the circumference of the base 601. The upper and lower flanges 602, 603 each have a diameter greater than the outer diameter of the base 601. The pressure regulation valve 60 is positioned, at its base 601, in a hole formed in the upper wall 506 of the bubble-breaking chamber 50. The upper and lower flanges 602, 603 help prevent the valve from being detached from the hole of the upper part 506.

When the gas-evacuation means is not operated, the pressure regulation valve 60 is in a state in which the lower flange 603 is in close contact with the inner surface of the upper part 506. On the other hand, when the gas-evacuation means is operated to reduce the pressure, a pressure difference arises between the interior and exterior of the bubble-breaking chamber 50. Due to this, the lower flange 603 warps or deflects at its edge so as to be spaced from the surface of the upper part 506. At this time, the interior of the bubble-breaking chamber 50 and the exterior of the bubble-breaking chamber 50 are communicated through the grooves 604 as shown in FIG. 10. This relaxes the pressure-reduced state in the bubble-breaking chamber 50.

By relaxing the pressure-reduced state, the first valve mechanism 5A (disk valve or lid 53) is suppressed (relaxed) from being drawn under pressure toward the bubble-breaking chamber 50 (first chamber 503), thus helping to facilitate relatively smooth opening and closing of the first valve mechanism 5A. By virtue of the smooth opening and closing of the first valve mechanism 5A, the float 20 coupled to the first valve mechanism 5A is allowed to move with relative swiftness and positiveness in response to a change in the liquid level H without being affected by the negative pressure. In the absence of this, the downward movement of the float 20 could be adversely affected (i.e., not as easily moved) because the first valve mechanism 5A is drawn under pressure toward the bubble-breaking chamber 50 and is thus inhibited from easily opening.

This also contributes to allowing the size of the float 20 acting to open and close the first valve mechanism 5A to be reduced.

The second valve mechanism 5B also can be relatively easily opened and closed similar to the first valve mechanism 5A. Due to this, the second valve 5B can be easily opened and closed in conjunction with the opening and closing of the first valve mechanism 5A.

The material of which the pressure regulation valve 60 is fabricated is not particularly limited. An example of a suitable material is natural rubber.

In the vicinity of the first gate 501, the first valve mechanism 5A is arranged to open and close the first gate 501. In the vicinity of the second gate 502, the second valve mechanism 5B is arranged to open and close the second gate 502.

The first valve mechanism 5A includes a movable valve member 53 which, in the illustrated embodiment, is in the form of a lid. The lid 53 is in a different location from the float 20 with reference to a horizontal plane. Accordingly, the lid 53 and the float 20 are connected together through a first link mechanism 16. With this arrangement, the lid 53 can be operated by the vertical movement of the float 20 in accordance with a change in the liquid level H as can be seen from a comparison of FIGS. 7-9.

In the illustrated embodiment, the lid 53 is in the form of a plate or a block. By closing the downward opening of the first gate 501 from below by the lid 53, the first gate 501 can be closed as shown in FIG. 7. On the other hand, moving the lid 53 away from the opening opens the first gate 501 as shown in FIG. 8.

With the first valve mechanism 5A constructed in this way, the first gate 501 reliably closes and opens by virtue of the movement of the lid 53 toward and away from the opening.

The first link mechanism 16 includes an arm 163 in the form of a rod. The arm 163 has one end 161 rotatably supported by the device body 40 and the other end 162 slidably supported to the float 20. The arm 163 has an intermediate portion 531 supporting the lid 53 at its center in a fixed fashion. When the float 20 moves vertically in accordance with a change in the liquid level H, the arm 163 rotates about the one end 161. By rotating the arm 163, the lid 53 is rotated about the one end 161 and is moved toward and away from the first gate 501. That is, the first valve mechanism 5A opens and closes at its first gate 501.

In the first valve mechanism 5A, when the liquid level H (the float 20 position at its shoulder 205, i.e., the boundary between its upper and intermediate portions 202, 204) rises and exceeds the first position S1, the lid 53 rotates counter-clockwise due to the rise of the float 20 so that the lid 53 moves toward (approaches) the first gate 501. This places the first gate 501 in a first state (closed state) as illustrated in FIG. 7. Conversely, when the liquid level H falls to the first position S1 or lower, the lid 53 rotates clockwise due to the fall of the float 20 and moves away from the first gate 501. This places the first gate 501 in a second state (opened state) shown in FIG. 8. When the liquid level H further falls (e.g., to a second position S2 lower than the first position S1), the lid 53 rotates clockwise due to the further fall of the float 20 into a position largely spaced from the first gate 501. Namely, the first valve mechanism 5A is opened to a greater degree than in the second state. Due to this, the first gate 501 is placed in a third state shown in FIG. 9.

The degree of opening of the first valve mechanism 5A in the second state, i.e., the inclination angle of the lid 53 relative to the horizontal, is not particularly limited, but is preferably 5-45 degrees, more preferably 15-30 degrees. The inclination angle in the third state is also not specifically limited, but is preferably 20-90 degrees, more preferably 25-45 degrees.

The material of which the lid 53 is fabricated is not limited to any particular material, but may be made of a resilient material similar to that of the pressure regulation valve 60. In this way, the first gate 501 is closed in a liquid-tight manner in the closed state (first state) of the first valve mechanism 5A.

The second valve mechanism 5B is adapted to open and close in conjunction with the opening and closing of the first valve mechanism 5A. The second valve mechanism 5B includes a resilient member 52 and a movable valve member 51 which, in the illustrated embodiment, is in the form of a needle member 51. The resilient member 52 is arranged at the inner periphery of the second gate 502. The material forming the needle member 51 is not especially limited, though it is possible to use a material such as mentioned above in connection with the explanation of the device body 40. The material forming the resilient member 52 is also not especially limited, though it is possible to use a material similar to that of the pressure regulation valve 60. Such a material forming the resilient member 52 can also be used as the material of the needle member 51. Where the needle member 51 is made of a resilient material, the resilient member 52 may be formed of a material greater in rigidity than the needle member 51 (e.g., such a material as mentioned in the description of the device body 40).

As shown in FIGS. 7-9, the needle member 51 is in a different location from the lid 53 (first valve mechanism 5A). That is, the needle member 51 is above the lid 53 (first valve mechanism 5A). For this reason, the needle member 51 and the lid 53 are coupled together through use of a second link mechanism 18. This helps ensure that the operation of the second valve 5B to open and close occurs in conjunction with the opening and closing of the first valve mechanism 5A.

The needle member 51 possesses an apex 511 that is conical (or pyramidal) in form. The resilient member 52 is in the form of a ring extending along the circumference of the inner periphery of the second gate 502. The second gate 502 is closed (i.e., positioned in either the first or second state) by positioning the apex 511 so that its outer peripheral surface is in close contact with the resilient member 52 as shown in FIGS. 7 and 8. The closed second gate 502 is opened (i.e., positioned in the third state) by moving the needle member so that the outer peripheral surface of the apex 511 becomes spaced from the resilient member 52 as illustrated in FIG. 9.

The construction of the second valve mechanism 5B thus helps facilitate opening and closing of the second gate 502 based upon the operation thereof.

The second link mechanism 18 has vertical and horizontal arms 181, 182 that are each in a rod form. The vertical arm 181 has one end (lower end) 183 rotatably supported by the lid 53. An elliptic (elongate) hole 184 is formed in the other end of the vertical arm 181 (upper end). The horizontal arm 182 has one end rotatably supported in the bubble-breaking chamber 50 and the other end 186 slidably supported in the hole 184 of the vertical arm 181. Meanwhile, the horizontal arm 182 has an intermediate portion where the needle 51 at its lower portion 512 is supported for rotation.

The second valve mechanism 5B is closed in the FIG. 7 state (first state) together with the first valve mechanism 5A. During the opening of the first valve mechanism 5A from the FIG. 7 closure state to a predetermined amount of opening, (i.e., reaching the FIG. 8 state which is the second state), the vertical arm 181 is pulled (moved) downwardly by the opening of the first valve mechanism 5A. At this time, because the horizontal arm 182 at the other end 186 slides in the hole 184 of the vertical arm 181, the other end 186 is maintained in its vertical position. That is, rotation of the horizontal arm 182 about the one end 185 does not occur. When the first valve mechanism 5A opens further from the FIG. 8 state, the horizontal arm 182 is pulled down by virtue of the other end 186 of the horizontal arm 182 abutting against the upper end of the hole 184. The arm 182 is thus rotated counterclockwise about the one end 185. This rotation causes the needle member 51 to move away from the resilient member 52 (second gate 502). As a result, the second valve mechanism 5B is opened and moved to the third state shown in FIG. 9.

Thus, during the opening of the first valve mechanism 5A from a closed state to a predetermined amount of opening, the vertical arm 181 is moved by the action of the second link mechanism 18, whereas the horizontal arm 182 is not rotated. That is, the second valve mechanism 5B is maintained in the closed state. Thereafter, the second valve mechanism 5B is opened together with the first valve mechanism 5A.

In other words, when the liquid level H is gradually lowered, the first valve mechanism 5A first opens, followed by opening of the second valve mechanism 5B. The second valve mechanism 5B thus opens with a delay relative to the first valve mechanism 5A.

In this manner, the second link mechanism 18 serves as a state-maintaining means for maintaining the second valve mechanism 5B in a closed state when the first valve mechanism 5A moves from the closed state (first state or starting state) to a predetermined degree of opening of the first valve mechanism 5A. An interaction mechanism is thus provided to produce a time difference in the opening/closure between the first and second valve mechanisms 5A, 5B. By virtue of the action of the second link mechanism 18, the bubble trap 1 is able to be positioned in the second and third positions. This properly sets the first and second valve mechanisms 5A, 5B with a proper timing and degree of opening/closing that is matched to the vertical position of the float 20 (i.e., the influx rate of bubbles). Therefore, the gas of the bubbles can be positively removed out of the device body 40 while the blood, making up the outer periphery of the bubbles, can be returned to the device body.

With the bubble trap 1 constructed in the illustrated and described example, when bubbles enter the device body 40 together with blood, the liquid level H changes in accordance with the influx rate of bubbles.

As shown in FIG. 7, in the state where there are incoming bubbles in an amount such that the liquid level H is not in the first position S1 or lower, the bubble trap 1 is in the first state shown in FIG. 7 in which the first gate 501 of the first valve mechanism 5A and the second gate 502 of the second valve mechanism 5B both remain closed. In this first state, the gas portion of the bubbles inside the device body 40 is only permitted to pass through the filter member 9, thus flowing into the passage 6 for the negative-pressure chamber 8. The gas entering the passage 6 passes through the check valve 30 and exits through the gas outlet port 81.

When the amount of bubbles entering the device body 40 cause the liquid level H in the interior of the device body 40 to be gradually lowered to the first position S1 or lower (i.e., when the amount of incoming bubbles is greater than in the case of the state shown in FIG. 7), the bubble trap is switched to the second state in which the second gate or opening 502 is maintained closed, but the first gate or opening 501 is opened by the downward movement of the float 20 and the action of the first valve mechanism 5A. In this second state, the bubbles in the device body 40 include those moving toward the filter member 9 as in the first state and those moving toward the first gate 501.

The bubbles moving toward the filter member 9 contact the filter member 9 and are broken so that the gas portion of the bubbles passes through the filter member 9 and the check valve 30 in that order and then exist through the gas outlet port 81 in a manner similar to that which occurs during the first state.

In addition, the bubbles moving toward the opened first gate 501 enter the first chamber 503 through the first gate 501. The bubbles entering the first chamber 503 contact the defoaming member 10 and are broken by the defoaming member 10, thus being separated into gas and blood. The gas moves up and is stored in the second chamber 504, while the blood moves down and returns into the device body 40 through the first gate 501.

At this point, if the second gate 502 were opened, the first chamber 503 (bubble-breaking chamber 50) could be under an excessively reduced pressure, thus possibly hindering the ability of the blood within the first chamber 503 to easily flow downward and return to the device body 40. However, in the illustrated and disclosed embodiment of the bubble trap 1, the second gate 502 is closed in the second state and so there is less likelihood, preferably no likelihood, that the first chamber 503 is under an excessively pressure reduced condition. Thus, the possibility that the return of blood from the first chamber 503 to the device body 40 will be hindered is not as likely to occur.

When the amount of bubbles entering the device body 40 causes the liquid level H to be gradually lowered from the first position S1 down to the second position S2 or lower (i.e., when the amount of incoming bubbles is greater than in the second state shown in FIG. 8), the first gate or opening 501 is opened more fully by the action of the first valve mechanism 5A, thus causing opening of the second gate or opening 502 by the action of the second valve mechanism. The bubble trap thus assumes the third state. In this third state, the bubbles within the device body 40 include those moving toward the filter member 9 and those moving toward the open first gate 501 in a manner similar to the second state.

The bubbles moving toward the filter member 9 are broken and the resulting gas passes through the filter member 9 and the check valve 30 in that order and then exits through the gas outlet port 81 in a manner similar to in the first and second states.

The bubbles moving toward the open first gate 501 move into the first chamber 503 through the open first gate 501. Here though, the amount of bubbles entering the first chamber 503 is greater than the amount of bubbles entering during the second state. The bubbles entering the first chamber 503 contact the defoaming member 10 and are broken by the defoaming member 10, thus being separated into gas and blood. The gas moves up in the second chamber 504 and enters the negative-pressure chamber 8 through the second gate 502. Thereafter, the gas is expelled or exhausted through the gas outlet port 81. The blood resulting from the broken bubbles flows down and returns to the device body 40 through the first gate 501. As mentioned above, in the third state of the bubble trap, the first valve mechanism 5A has an opening degree greater than that of the second state. Because the first gate 501 (first valve mechanism 5A) is opened to an extent capable of eliminating (relaxing) the pressure-reduction state within the first chamber 503, the blood positively flows down and returns to the device body 40.

This illustrated and disclosed embodiment of the bubble trap 1 is well suited to separating the bubbles contained in the blood circulated extracorporeally into gas and blood, and is able to remove the gas with efficiency and positiveness irrespective of the influx rate of bubbles into the bubble trap 1.

When the bubble trap 40 is in the third state and the liquid level H within the device body 40 gradually rises and exceeds the second position S2 due to a decrease in the influx rate of bubbles, the second valve mechanism 5B first closes and then the first valve mechanism 5A closes (or the second valve mechanism 5B closes nearly simultaneously with the first valve mechanism 5A) through the action of the second link mechanism 18 which acts to produce a time difference in opening/closure between the first and second valve mechanisms 5A, 5B. This provides an advantage that blood is prevented from entering the bubble-breaking chamber 50 as a result of a cut-off of the pressure reduction within the bubble-breaking chamber 50, and further the blood within the bubble-breaking chamber 50 is able to return to the device body 40.

The bubble trap 1 in this embodiment is described as being shifted from the first state, to the second state and then to third state in that order. However, under certain conditions of blood flow, the bubble trap 1 may, for example, shift from the first state to the second state and then back to the first state.

According to the various illustrated and described embodiments, the filter member is arranged along a first communication path between the interior of the device body and the gas outlet port and this filter member permits the passage of the gas portion of the bubbles while preventing passage of the blood portion of the bubbles. In addition, a gate or opening is positioned along a second communication path between the interior of the device body and the gas outlet port that is different from the first communication path. This opening is adapted to be opened and closed by the movable valve member that is movable between a closed position in which the movable valve member closes the opening to prevent flow through the opening and an open position in which flow through the opening is permitted. The valve member is connected to the float that is positioned in the interior of the device body, with the float being vertically movable in response to changes in the blood level in the device body which occurs as result of changes in the amount of bubbles entering the interior of the device body.

The principles, preferred embodiments and modes of operation have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method of removing bubbles in an extracorporeal circuit comprising:
   introducing blood from a patient into an interior of a device body;
   contacting bubbles in the blood with a filter member to break the bubbles into gas and blood;
   operating a negative-pressure source to draw the gas out of a gas outlet port of the device body along a first communication path when a level of blood in the interior of the device body is above a predetermined blood level;
   providing a second communication path different from the first communication path, the second communication path being provided with an opening that is closed when the level of blood in the interior of the device body is above the predetermined blood level;
   opening the closed second communication path opening when the level of blood in the interior of the device body is below the predetermined blood level;
   contacting bubbles in the blood passing through the second communication path with a defoaming member to break the bubbles into gas and blood; and
   drawing the gas produced by contact of the bubbles with the defoaming member along the second communication path through operation of the negative-pressure source;
   wherein gas is drawn out of the gas outlet port of the device body along the first communication path when the level of blood in the interior of the device body is above the predetermined blood level;
   wherein gas is drawn out of the gas outlet port of the device body along both the first communication path and the second communication path when the level of blood in the interior of the device body is below the predetermined blood level; and
   wherein the opening is a first opening along the second communication path, wherein a second opening is positioned along the second communication path and is closed when the level of blood in the interior of the device body is above a different blood level that is different from the predetermined blood level, the method further comprising opening the second opening when the level of blood within the interior of the device body is below the different blood level.

2. The method according to claim 1, wherein the bubbles contact the defoaming member after passing through the opening.

3. The method according to claim 1, wherein the bubbles contact the defoaming member before passing through the opening.

4. The method according to claim 1, wherein the different blood level is vertically above the predetermined blood level and the second opening is opened before the first opening is opened.

* * * * *